United States Patent
Deckard

(10) Patent No.: US 7,555,936 B2
(45) Date of Patent: Jul. 7, 2009

(54) HYDRAULIC HOSE WITH INTEGRAL LIFE-SENSING CAPABILITY AND METHOD THEREFOR

(75) Inventor: Aaron Don Deckard, Lexington, KY (US)

(73) Assignee: Purdue Research Foundation, West Lafayette, IN (US)

( * ) Notice: Subject to any disclaimer, the term of this patent is extended or adjusted under 35 U.S.C. 154(b) by 422 days.

(21) Appl. No.: 11/276,500

(22) Filed: Mar. 2, 2006

(65) Prior Publication Data

US 2006/0196252 A1 Sep. 7, 2006

Related U.S. Application Data

(60) Provisional application No. 60/658,932, filed on Mar. 4, 2005.

(51) Int. Cl.
*F16L 55/00* (2006.01)
(52) U.S. Cl. .............. 73/49.5; 73/40; 73/49.1; 73/49.2; 73/763; 138/104; 138/127; 702/35; 702/185
(58) Field of Classification Search ................ 73/49.5; 138/104, 127
See application file for complete search history.

(56) References Cited

U.S. PATENT DOCUMENTS

| | | |
|---|---|---|
| 3,555,887 A | 1/1971 | Wood |
| 3,603,142 A | 9/1971 | Saylak et al. |
| 3,906,340 A | 9/1975 | Wingfield et al. |
| 4,029,889 A | 6/1977 | Mizuochi |
| 4,446,892 A | 5/1984 | Maxwell |
| 5,343,738 A | 9/1994 | Skaggs |
| 5,551,484 A | 9/1996 | Charboneau |
| 5,634,497 A | 6/1997 | Neto |
| 5,966,018 A | 10/1999 | Edmunds et al. |
| 5,969,618 A | 10/1999 | Redmond |
| 5,992,218 A | 11/1999 | Tryba et al. |

(Continued)

FOREIGN PATENT DOCUMENTS

EP 0185650 6/1986

(Continued)

OTHER PUBLICATIONS

Sergio, M. et al., "On Road Tire Deformation Measurement System Using a Capacitive-Resistive Sensor", IEEE, 2003, pp. 1059-1063.*

*Primary Examiner*—Daniel S Larkin
(74) *Attorney, Agent, or Firm*—Hartman & Hartman, P.C.; Gary M. Hartman; Domenica N. S. Hartman

(57) ABSTRACT

A system and method for predicting structural failure of a wall of a fluid containment vessel, such as a hydraulic hose or other type of pressurized conduit of types used in mobile machinery, automotive, aerospace, manufacturing, and process equipment. The wall of the vessel has an innermost layer for contact with the fluid contained by the vessel, and an outermost layer parallel with the innermost layer. The system includes strain-sensing means between the innermost and outermost layers and comprising at least one conductor parallel to the innermost layer of the wall. The system and method entail sensing changes in an electrical property associated with the at least one conductor resulting from distortion of the wall of the vessel causing distortion of the at least one conductor.

33 Claims, 3 Drawing Sheets

U.S. PATENT DOCUMENTS

| | | |
|---|---|---|
| 6,361,299 B1 | 3/2002 | Quigley et al. |
| 6,386,237 B1 | 5/2002 | Chevalier et al. |
| 6,498,991 B1 | 12/2002 | Phelan et al. |
| 6,958,615 B2 | 10/2005 | Poulbot et al. |
| 2003/0164048 A1 | 9/2003 | Shkel |
| 2004/0045365 A1 | 3/2004 | Richardson |

FOREIGN PATENT DOCUMENTS

| | | |
|---|---|---|
| EP | 185650 | 6/1986 |
| EP | 0892244 | 1/1999 |
| GB | 1570511 | 7/1980 |

\* cited by examiner

HYDRAULIC HOSE WITH INTEGRAL LIFE-SENSING CAPABILITY AND METHOD THEREFOR

CROSS REFERENCE TO RELATED APPLICATIONS

This application claims the benefit of U.S. Provisional Application No. 60/658,932, filed Mar. 4, 2005, the contents of which are incorporated herein by reference.

BACKGROUND OF THE INVENTION

The present invention generally relates to vessels that contain static or flowing fluids, including conduits such as hydraulic hoses of the types used in mobile machinery, automotive, aerospace, manufacturing, and process equipment. More particularly, this invention relates to hydraulic hoses equipped with means for sensing the life of the hose in terms of wear, fatigue, and/or other structural breakdown of its components, and means for electrically monitoring the hose to predict a structural failure.

Interest exists in developing methods for consistently predicting the failure of vessels containing fluids, including but not limited to hoses, thereby enabling replacement or repair of the vessel before failure. For example, U.S. Pat. No. 5,634,497 to Neto, U.S. Pat. No. 6,386,237 to Chevalier et al., and U.S. Pat. No. 6,498,991 to Phelan et al. disclose the detection of a worn hose by sensing the electrical resistivity in one or more wires embedded in the wall of the hose. These patents focus on detecting a discontinuity in the embedded wires, such as would result from breakage of the wires due to wear as opposed to sensing a gradual increase in resistivity attributable to wear or deformation of the hose or its wires.

U.S. Pat. No. 5,343,738 to Skaggs differs by disclosing a method for capacitively sensing the failure of a hose. In Skaggs, a fuel leakage through an inner layer of a hose is sensed on the basis of the leaked fuel altering the dielectric properties of an insulating material between a pair of copper wires embedded in the hose. Similar to Skaggs, U.S. Pat. No. 5,992,218 to Tryba et al. discloses sensing water leakage through a hose on the basis of the leaked water increasing the conductivity of an electrical insulating layer between a pair of conductor layers separated by the insulating layer. U.S. Pat. No. 5,969,618 to Redmond also discloses a method for detecting the failure of a hose on the basis of electrical conductivity. Redmond's hose is formed to have an annulus containing separated wires, and the failure of the inner layer of the hose is sensed when fluid leaks into the annulus and closes an electric circuit containing the wires.

Another approach to sensing an impending failure of a hose is disclosed in U.S. Pat. No. 4,446,892 to Maxwell. Maxwell discloses a fluid (oil) transport hose formed by at least two plies and a sensing element therebetween. In one embodiment of Maxwell, the sensing element is responsive to the electromagnetic properties of fluid present between the plies as a result of a failure of an inner ply of the hose. In a second embodiment of Maxwell, the sensing element is responsive to the failure of an inner ply of the hose by presenting an open circuit. The sensing element is said to preferably be a coil of fine wire wrapped around the inner ply and connected to means responsive to changes in the electrical impedance (AC) of the coil. Such changes are said to occur from fluid seepage into the material contacting with the coil or deformation of the inner ply, both of which change the inductance of the coil. In an alternative embodiment in which the sensing element is primarily intended to be responsive to the seepage of fluid (oil) between the plies of the hose, Maxwell employs parallel non-touching wires connected to means responsive to a change in conductance between the individual wires or to a change in the capacitance between the wires.

The prior art discussed above is particularly concerned with conduits through which a fluid is conveyed from one location to another, as opposed to fluid conduits such as hydraulic hoses in which little flow actually occurs and structural fatigue of the wall from pressure cycles is an important factor in hose life. Furthermore, sensing systems of the type suggested by Maxwell are generally useful in relatively low pressure systems where the detection of seepage within the hose wall could provide an adequate warning of impending failure. However, in high pressure fluid components such as hydraulic hoses, once seepage occurs catastrophic failure is likely to occur in a matter of seconds, not hours or even minutes. Therefore, it would be desirable if a method and hose design were available that made it possible to not only sense an imminent fatigue failure of a hydraulic hose, but were also capable of predicting when a structural failure of the hose will occur so that the hose can be safely used for its full life and then replaced before any damage occurs to the fluid system containing the hose or the apparatus employing the hose.

BRIEF SUMMARY OF THE INVENTION

The present invention provides a system and method for predicting structural failure of a wall of a fluid containment vessel, such as a hydraulic hose or other type of pressurized conduit of types used in mobile machinery, automotive, aerospace, manufacturing, and process equipment. In contrast to prior art failure detection systems, the invention is adapted to provide an indication of localized yielding anywhere in the vessel wall, from which a warning of a catastrophic failure of the wall can be provided minutes if not hours before failure occurs.

According to the invention, the wall of the fluid containment vessel has an innermost layer for contact with the fluid contained by the vessel, and an outermost layer parallel with the innermost layer. The system includes strain-sensing means between the innermost and outermost layers and comprising at least one conductor parallel to the innermost layer of the wall. The system further includes means for sensing changes in an electrical property associated with the at least one conductor resulting from distortion of the wall of the vessel causing distortion of the at least one conductor. The method of this invention entails forming the wall to contain between its innermost and outermost layers a strain-sensing means having at least one conductor parallel to the innermost layer of the wall, and then sensing changes in an electrical property associated with the at least one conductor resulting from distortion of the wall of the vessel causing distortion of the at least one conductor.

The strain-sensing means and step preferably operate on the basis of either electrical capacitance or electrical resistance (DC). According to a first aspect of the invention, the change being sensed is a change in an electrical capacitance between the at least one conductor and a second conductor of the strain-sensing means, which according to this embodiment results from yielding of the vessel wall. According to a second aspect of the invention, the change sensed is a change in the electrical resistance (DC) of the at least one conductor, which in this embodiment also results from yielding of the vessel wall. According to a preferred aspect of the invention, an acceptable range is established for the electrical property, and a signal is generated that a structural failure of the wall is impending in response to the electrical property deviating outside the acceptable range.

An important feature of the invention is that electrical monitoring of a fluid containment vessel as described above, and particularly monitoring electrical capacitance with respect to a preestablished acceptable range, has been shown to enable accurate predictions of wall failure as a result of electrical changes being generally nominal until an abrupt electrical change occurs that sufficiently precedes failure to enable repair of the wall or replacement of the vessel before any harm occurs to the system or apparatus in which the vessel is used. In this regard, the electrical property being sensed is capable of indicating distortion of the vessel wall resulting from fatigue, and not internal leakage or other actual structural failure within the vessel wall that would lead to an almost immediate catastrophic failure.

Other objects and advantages of this invention will be better appreciated from the following detailed description.

DETAILED DESCRIPTION OF THE INVENTION

The invention involves creating an electrical circuit within a wall of a fluid containment vessel, such as a hydraulic hose, and sensing changes in an electrical property responsive to distortion of the wall, evidencing wear, fatigue, and/or other structural breakdown of the vessel. According to preferred embodiments of the invention, the electrical property of interest is capacitance or resistance, and conductive, dielectric, and/or resistive layers are formed as necessary to create an electrical capacitor and/or resistor within the wall of the vessel, by which changes in capacitance and/or resistance are sensed.

Figure 1:
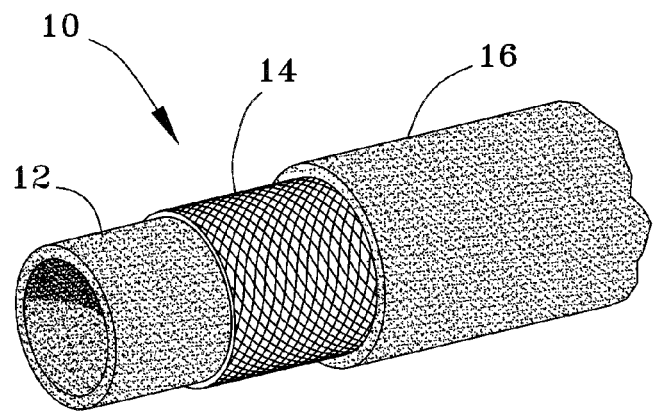
FIG. 1 represents a hydraulic hose of a type known in the art, with layers of the hose exposed to show the hose construction.

A hose 10 of a type known in the art is represented in FIG. 1. The hose 10 is representative of various types of hoses that may be used to contain a flowing or static fluid. A particular example is a hydraulic hose that contains a hydraulic fluid whose pressure fluctuates. The hose 10 is represented as having an inner tube 12 that contacts a fluid flowing through the hose 10, a reinforcement layer 14 that strengthens the hose 10, and an outer cover 16 that protects the hose 10 and its interior components. Because the inner tube 12 directly contacts the fluid, the material from which the inner tube 12 is formed must be chemically compatible with the fluid contained by the hose 10. As a result, various materials have been employed for the inner tube 12, including nitrile-butadiene, chloroprene, copolymer of ethylene and propylene, polytetrafluoroethylene (PTFE), etc. The reinforcement layer 14 promotes the strength of the hose 10. Any number of reinforcement layers 14 may be present in the hose 10, and reinforcement layers 14 have been constructed from a variety of materials in a variety of configurations. Typical materials include metals such as steels, bronze, and aluminum, synthetic materials such as rayon, nylon, polyethylene terephthalate (PET) fiber, and glass fiber, and textile yarns such as cotton. If multiple reinforcement layers 14 are used, rubber separation layers may be placed between the reinforcement layer 14 to reduce abrasion and wear therebetween. Suitable materials for the outer cover 16 will depend on the operating environment of the hose 10, with typical materials including synthetic rubbers.

It is conventional to equip the ends of the hose 10 with fittings (not shown) to permit connection of the hose 10 to other hoses or equipment in the system containing the hose 10. Typical fittings include a nipple that is forced into the opening of the inner tube 12, and an outer collar or socket that is crimped onto the exterior of the hose 10 and a portion of the nipple protruding from the hose 10. The socket is typically equipped with barbs that are forced through the outer cover 16 and into the reinforcement layer 14 during crimping to secure the fitting on the hose 10. Close tolerances are required to achieve a fluid-tight seal between the hose 10 and the fitting, resulting in a wide variety of fittings in various sizes.

Hydraulic hoses of the type represented in FIG. 1 fail by a variety of mechanisms, including abrasion, loading, fatigue, and environmental factors relating to the hose as well as its fittings. Because hydraulic hoses are often subject to cyclic loading as a result of pressure changes during startup, shutdown, and normal operation of a hydraulic system, fatigue is an important factor in the life of hydraulic hoses and their fittings. The fatigue rate can increase markedly as a result of damage to the inner tube 12, reinforcement layer 14, and outer cover 16 of the hose 10, or to the hose fittings.

Figure 2:
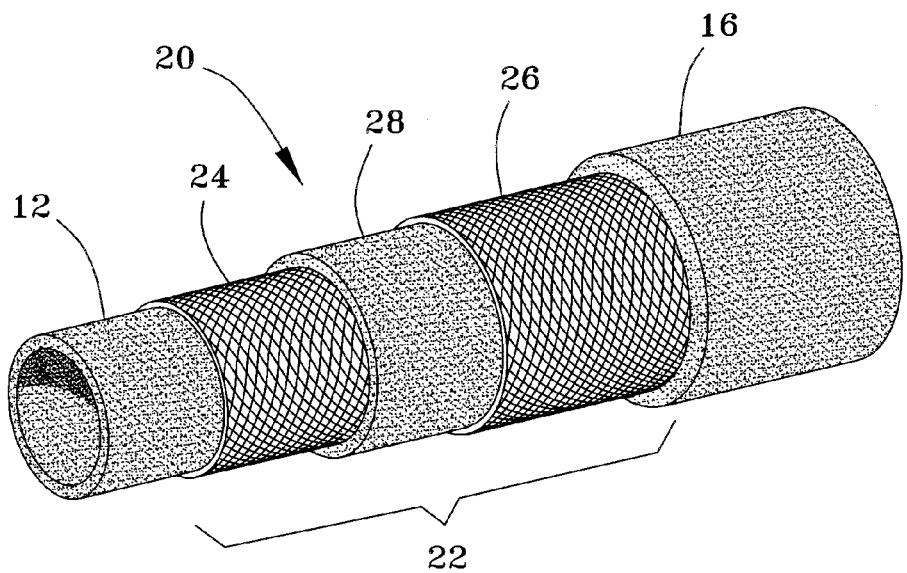
FIG. 2 represents a hydraulic hose configured to have a strain-sensing layer in accordance with a first embodiment of the present invention, with layers of the hose exposed to indicate the hose construction.
Figure 3:
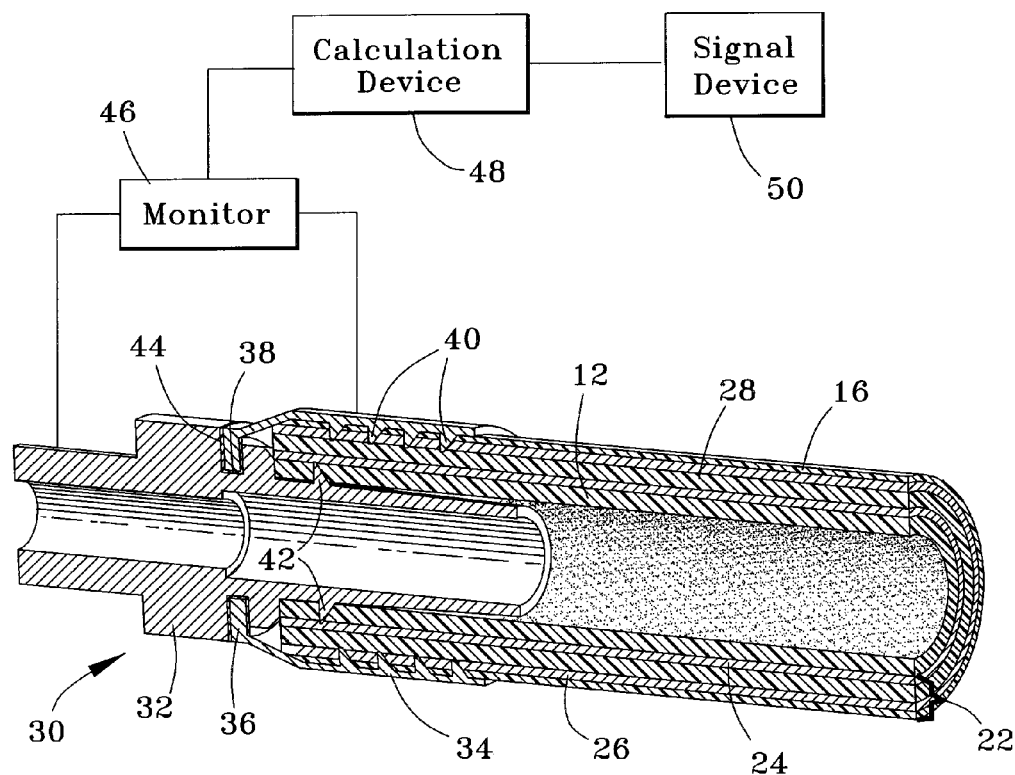
FIG. 3 shows a fitting of a type for use with the hydraulic hose of FIG. 2 in accordance with a preferred embodiment of this invention.

FIGS. 2 and 3 represent a hydraulic hose 20 according to a first embodiment of the invention. Similar to the hose 10 of FIG. 1, the hose 20 has an inner tube 12 and an outer cover 16. Both of these components of the hose 20 are formed of electrically insulating materials, such as those materials noted above for the hose 10 in FIG. 1. However, in place of the reinforcement layer 14 of FIG. 1, the hydraulic hose 20 contains a multilayer strain-sensing structure 22 between the inner tube 12 and outer cover 16. In the embodiment of FIGS. 2 and 3, the strain-sensing structure 22 operates on the basis of electrical capacitance. The strain-sensing structure 22 is shown as comprising an inner conductive layer 24 surrounding the inner tube 12, an electrical insulating layer 28 surrounding the inner conductive layer 24, and an outer conductive layer 26 surrounding the insulating layer 28 and separated from the inner conductive layer 24 by the insulating layer 28 to define a capacitive coupling comprising the inner conductive layer 24, the insulating layer 28, and the outer conductive layer 26. The capacitance of the capacitive coupling can be calculated with the following equation.

$$C = 2\pi \epsilon L / \ln(b/a)$$

where C is capacitance in farads, $\epsilon$ is the dielectric permittivity of the material of the insulating layer 28 (related to the dielectric constant of the material), L is the length of the capacitor coupling within the hose 20, a is the radius of the inner conductive layer 24, and b is the radius of the outer conductive layer 26. According to the invention, for a unit length L of the hose 20, the radii of the inner and outer conductive layers 24 and 26 (a and b, respectively), the ratio b/a, and the dielectric constant (permittivity) of the insulating layer 28 will change as the hydraulic hose 20 fatigues. The hose 20 permanently strains due to fatigue, resulting in increases in the radii of the inner and outer conductive layers 24 and 26. Because the outer cover 16 tends to constrain the interior of the hose 20, any increase in the radii of the inner and outer conductive layers 24 and 26 tends to decrease the distance between the inner and outer conductive layers 24 and 26, corresponding to a decrease in the thickness of the insulating layer 28. As the hose 20 fatigues, changes in the dielectric constant are believed to occur, as do the physical properties of the layers 24, 26, and 28 that can also affect the capacitance of the capacitive coupling.

Suitable materials for the conductive layers 24 and 26 include reinforcement braiding as represented in FIG. 2. As examples, suitable materials include metal wires such as steels, bronze, and aluminum used for prior art reinforcement materials, though it is foreseeable that other electrically conductive materials could be used. A variety of materials can be used for the insulating layer 28, with a preferred material being silicone rubber. As evident for the capacitance equation discussed above, the ratio of the radii of the inner and outer conductive layers 24 and 26 and the thickness of the insulating layer 28 are important to ensure an appropriate level of electrical insulation for the capacitive coupling.

In an investigation leading to the present invention, hydraulic hoses similar to that represented in FIG. 2 were fabricated based on a commercial product with part number FC212 manufactured by Aeroquip. Each hose was constructed to have a synthetic nitrile rubber inner tube 12 with an inner diameter of about one-half inch (about 13 mm) and a wall thickness of about 0.05 inch (about 1.3 mm), steel wire braid inner and outer conductive layers 24 and 26 with wall thicknesses of about 0.03 inch (about 0.8 mm), an insulating layer formed of an SE860 silicone rubber material commercially available from GE Silicones and having a wall thickness of about 0.075 inch (about 1.9 mm), and an outer cover 16 extruded onto the outer conductive layer 26 to have a wall thickness of about 0.05 inch (about 1.3 mm). Each hose had an outer diameter of about 0.946 inch (about 24.0 mm) and an overall wall thickness of about 0.235 inch (about 6.0 mm). While the hoses were constructed of particular materials and with the particular dimensions noted above, it is within the scope of this invention that other materials and dimensions could have been used. A notable characteristic of silicone rubber is swelling when exposed to oil, such that an insulating layer 28 formed of silicone rubber will tend to force the conductive layers 24 and 26 apart if the inner tube 12 and conductive layers 24 and 26 are breached, resulting in a notable change in the capacitance of the capacitive coupling.

Electrical connection to the inner and outer conductive layers 24 and 26 of each hose was through fittings specifically configured for this purpose. In FIG. 3, a fitting 30 is shown that is similar in construction to fittings used in the past with hydraulic hoses, for example, a Global TTC-type fitting available from Aeroquip. The fitting 30 includes a nipple 32 adapted to be forced into the opening of the inner tube 12, and a socket 34 that is crimped onto the exterior of the hose 10. The socket 34 is equipped with a crimp ring 36 that engages a channel 38 on the nipple 32 to firmly secure the socket 34 to the nipple 32. The socket 34 is further equipped with barbs 40 that are forced through the outer cover 16 and into the outer conductive layer 26 during crimping. In the embodiment of FIG. 3, the barbs 40 are defined by four concentric rings on the socket 34 and have heights of about 0.060 inch (about 1.5 mm). The nipple 32 differs from conventional fittings by further having one or more barbs 42 that are sufficiently sharp to penetrate through the inner tube 12 and into the inner conductive layer 24 during assembly and crimping of the hose 20 and fitting 30. A sufficient number of barbs 42 should be present on the nipple 32 to promote the strength of the connection between the nipple 32 and hose 20 while also providing a reliable seal between the nipple 32 and inner tube 12 of the hose 20. In view of the latter consideration, it was determined that a single barb 42 circumscribing the nozzle 32 and having a height of about 0.066 inch (about 1.7 mm) was well suited. Finally, an insulator 44 is present between the ring 36 and channel 38 of the socket 34 and nipple 32 so that these components of the fitting 30 are electrically insulated from each other. In the investigation, the insulator 44 was formed of a polyolefin material commercially available from Raychem Corporation under the name Thermofit RNF-100.

With the above construction, electrical connection was made to the inner and outer conductive layers 24 and 26 of each hose through the nipple 32 and socket 34, respectively, of the fittings 30. By providing an appropriate monitor 46, changes in the electrical capacitance of the capacitive coupling (formed by the inner conductive layer 24, the insulating layer 28, and the outer conductive layer 26) can therefore be sensed. According to the invention, such changes are believed to occur as a result of permanent distortions (plastic deformation) occurring within the wall of the hose 10. In the investigation, such distortions were intentionally induced by cycling hoses according to the above description at a rate of about sixty cycles per minute with a 10W30 motor oil at pressures between 0 and 2300 psi (about 15.8 MPa). The monitor (46 in FIG. 3) employed in the investigation was a Hewlett Packard 4263B LCR meter. The test pressure range was initially chosen on the basis of using a maximum pressure of not more than one-quarter of the burst pressure, which was determined to be about 12000 psi (about 82.7 MPa) for the hose design evaluated. However, after 78,000 cycles, no visual signs of fatigue were observed, and the decision was made to increase the maximum pressure to about 2800 psi (about 19.3 MPa) for the following hour of cycling and then to increase the pressure by about 500 psi (about 3.45 MPa) every hour thereafter. With this schedule, the first failure occurred at 3800 psi, and a second failure followed shortly.

Figure 5:
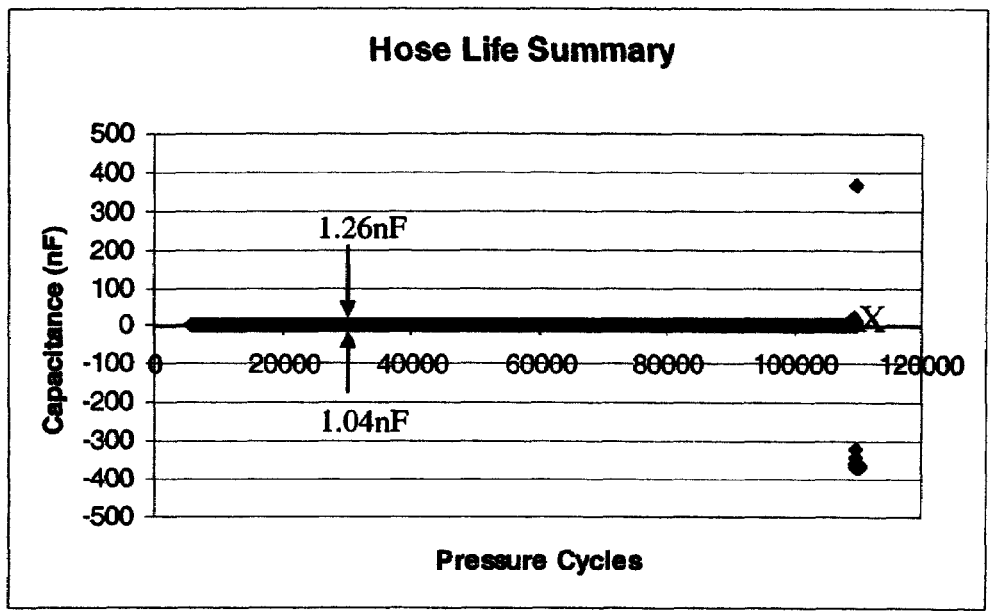
FIGS. 5 and 6 are plots of data obtained from testing a hose of the type shown in FIGS. 2 and 3.
Figure 6:
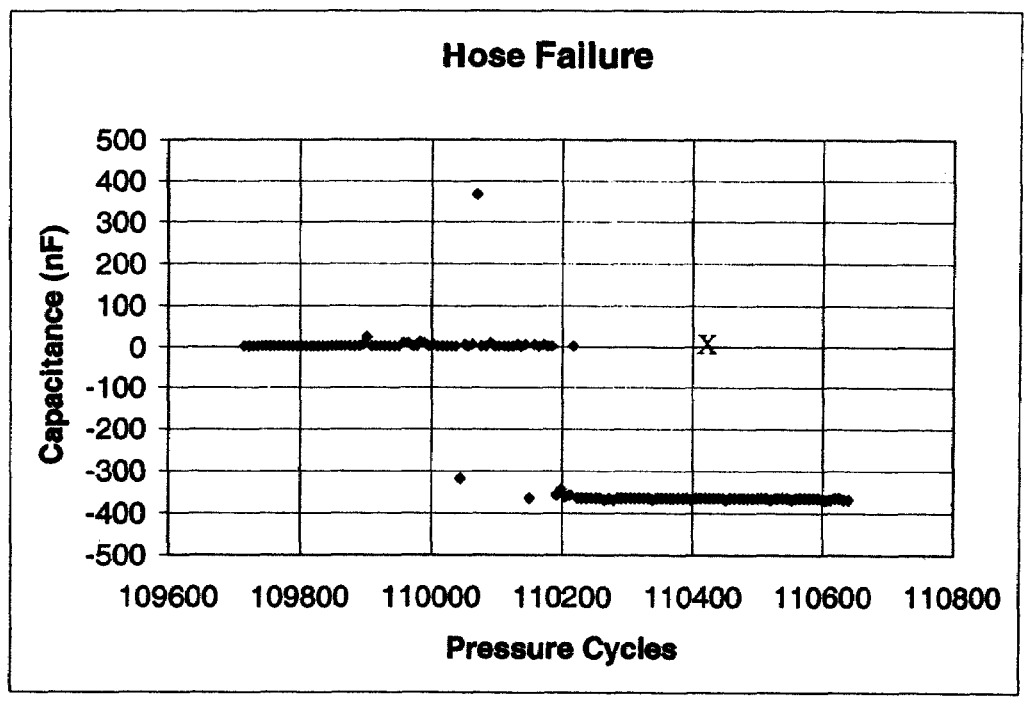

FIGS. 5 and 6 represent plots of data obtained from one of the tested hoses. In FIGS. 5 and 6, capacitance (in nF) is plotted against pressure cycles, with FIG. 5 plotting data obtained over the entire test life of the hose, while FIG. 6 is limited to the cycles immediately proceeding failure of the hose, which occurred at 110,428 cycles (indicated by an X in FIGS. 5 and 6). From startup until about 108,000 cycles, the capacitance value of the capacitive coupling within the hose remained in a range of about 1.04 nF to about 1.26 nF, reflecting changes in capacitance attributable to elastic deformation of the hose and its internal layers. At about 108,000 cycles, the readings began to fluctuate on orders of magnitude of about 300 times or greater until failure occurred. The negative capacitance values observed were attributed to the conductive layers of the capacitive coupling contacting each other. The maximum capacitance value abruptly increased to about 22.5 nF at about 109,902 cycles, which preceded failure of the hose by 526 cycles.

The other hoses prepared for this investigation were tested under identical conditions and found to perform similarly, with capacitance abruptly changing at least 100 cycles before failure. Testing of one specimen was terminated when its fitting failed, an event that notably was immediately detected because the electrical connection to the capacitive coupling was lost. Excluding the specimen with the failed fitting, five specimens tested in the manner described above had an average time between an abrupt capacitance reading and hose failure of about 339 cycles. The abrupt changes observed in capacitance varied between about four and about seventy-eight times greater than the initial mean capacitance readings for their respective hoses. Such results were concluded to indicate that an impending failure of a hose can be anticipated based on capacitance readings exceeding the upper limit of a range calculated from an initial reading obtained with the hose, for example, a range extending up to about three times the initial capacitance reading of the hose.

The above results evidenced that failure of a hydraulic hose subjected to pressure cycling could be predicted by monitoring the capacitance value of an appropriate capacitive coupling within the hose, with sufficient warning to enable the hose to be replaced before failure actually occurs. For this purpose, a suitable system for carrying out this invention includes, in addition to the monitor 46 indicated in FIG. 3, a device 48 to calculate an acceptable range for the electrical capacitance of the capacitive coupling (e.g., based on an initial capacitance reading obtained from the hose), and a device 50 that generates a visual and/or audible signal that a structural failure of the hose 20 is impending in view of the capacitive value deviating outside the acceptable range.

Figure 4:
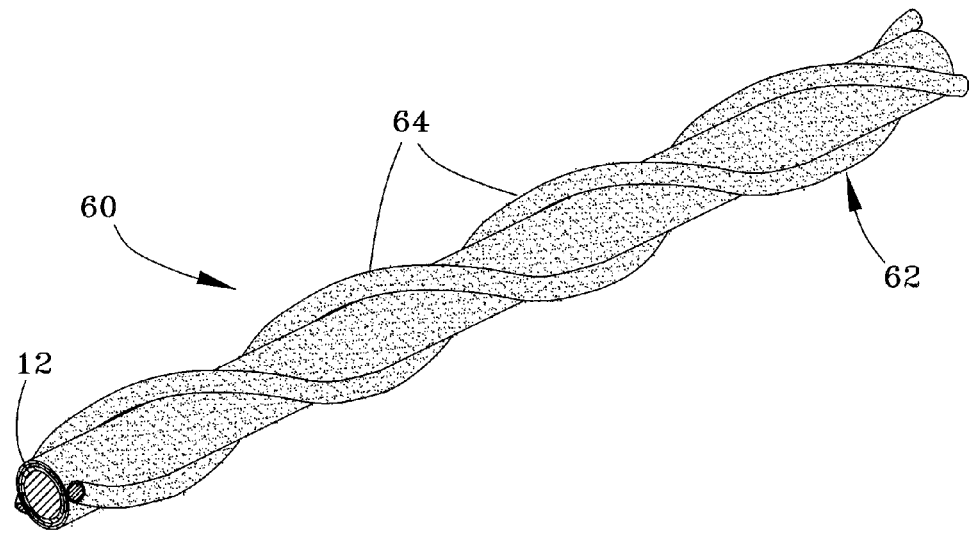
FIG. 4 represents a hydraulic hose configured in accordance with a second embodiment of the present invention, with an exterior portion of the hose removed to show a strain-sensing layer within the hose.

FIG. 4 represents the interior structure of a hydraulic hose 60 according to a second embodiment of the invention. Similar to the hoses 10 and 20 of FIGS. 1 and 2, the hose 60 has an inner tube 12 that can be protected by an outer cover (not shown). Furthermore, the hose 60 may include a reinforcement layer (not shown) between the inner tube 12 and the outer cover. Suitable materials for these layers include those noted above for the corresponding layers of the hoses 10 and 20. However, in place of the conductive layers 24 and 26 and insulating layer 28 that make up the multilayer strain-sensing structure 22 of FIG. 2, the hose 60 of this embodiment has a strain-sensing structure 62 that may comprise one or more conductors 64 that surround the inner tube 12 to form one or more electrically isolated helical conductive paths along the length of the hose 60. According to this embodiment of the invention, the strain-sensing structure 62 operates on the basis of electrical resistance, and an impending failure of the hose 60 can be predicted by observing changes in the resistance of the conductor 64. The resistance of the conductor 64 can be calculated with the following equation.

$$R = \rho L/A$$

where R is resistance in ohms, $\rho$ is resistivity of the material of the conductor 64, L is the length of the conductor 64, and A is the cross-sectional area of the conductor 64. As the hose 60 permanently strains due to fatigue, the result is an increase in the radius of the inner tube 12 around which the conductor 64 is wrapped, causing the length of the conductor 64 to increase and the cross-sectional area of the conductor 64 to decrease, both of which lead to an increase in the resistance of the conductor 64 in accordance with the above equation. From the equation, it can be appreciated that greater resistivities and lengths and lesser cross-sectional areas for the conductor 64 promote higher resistances that can increase the sensitivity of the strain-sensing layer 62 to plastic deformation of the hose 60.

The conductor 64 may be formed of a metal or a conductive polymer, with conductive polymers potentially being preferred because their increased resistivity compared to metals may increase the degree to which resistance will change resulting from a given amount of deformation in the hose 60. If multiple conductors 64 are used, each is insulated from the others with one or more electrical insulating layers (not shown).

As with the embodiment of FIGS. 2 and 3, electrical connection to the conductor 64 can be made through a fitting of the type used to connect the hose 60 to another hose or other member of a hydraulic system. In contrast to the embodiment of FIGS. 2 and 3, a suitable fitting can provide electrical connection to the conductor 64 from either the exterior or interior of the hose 60. As such, a fitting similar to that in FIG. 3 can be used, but with the barbs 42 on the nipple 43 being unnecessary. As a result, the fitting can be similar in construction to fittings used in the past with hydraulic hoses, such as an Aeroquip Global TTC-type fitting.

In an investigation of the embodiment of FIG. 4, hoses were constructed with the same inner tube material and size as used in the investigation of the previous embodiment. Each inner tube was overlap wrapped with a bi-layer ribbon formed of a sheet of filled silicone conductor on a sheet of polyethylene insulator. The silicone conductor had a thickness of about 0.040 inch (about 1 mm), and the insulator had a thickness of about 0.001 inch (about 0.025 mm). The width of the bi-layer ribbon was about two inches (about 51 mm). Because the hoses lacked a reinforcement layer, the burst pressure of this hose configuration was determined to be only about 277 psi (about 1.9 MPa), much lower than that for the hoses tested with the previous embodiment. As such, though pressure cycling was again employed to evaluate hoses of this embodiment, lower pressures were used. The cycle rate was about sixty cycles per minute with a 10W30 motor oil as the hydraulic fluid. Resistance was monitored with the same Hewlett Packard 4263B LCR meter as used in the previous investigation. The initially chosen test pressure range was 0 to about 60 psi (about 0.41 MPa), again on the basis of using a maximum pressure of not more than one-quarter of the burst pressure. However, to expedite the fatigue process, the maximum pressure was increased to about 80 psi (about 0.55 MPa) after 25,140 cycles, and then further increased to about 100 psi (about 0.69 MPa) through the completion of testing of each hose specimen.

Six hoses were evaluated in the investigation, with cycles to failure ranging from 22,025 to 33,556 cycles. Excluding one sample due to wide fluctuations in readings, the average increase in resistance from initial to immediately prior to failure ranged from about 6.45% to about 34.2%. Unfortunately, failures of specimens tended to interfere with data collection of specimens still on test as a result of the manner in which the specimens were electrically monitored. More significantly, changes in resistance for all specimens were gradual over the entire duration of the test with the result that prediction of failure would be difficult with the specimens as constructed. However, it is foreseeable that better results capable of providing a degree of prediction capability might be obtained with a different hose design.

While the invention has been described in terms of a preferred embodiment, it is apparent that other forms could be adopted by one skilled in the art. For example, the physical configuration of the hoses and fittings could differ from those shown, and materials and processes other than those noted could be use. Therefore, the scope of the invention is to be limited only by the following claims.

The invention claimed is:

1. A system for predicting structural failure of a wall of a fluid containment vessel, the wall having an innermost layer for contact with a fluid contained by the vessel and an outermost layer parallel with the innermost layer, the system comprising:

strain-sensing means between the innermost and outermost layers, the strain-sensing means comprising at least one conductor parallel to the innermost layer of the wall;

means for sensing changes in an electrical property associated with the at least one conductor resulting from distortion of the wall of the vessel causing distortion of the at least one conductor, the electrical property being chosen from the group consisting of electrical capacitance and electrical resistance;

means for establishing an acceptable range for the electrical property; and means for generating a signal that a structural failure of the wall is impending in response to the electrical property deviating outside the acceptable range.

2. A system according to claim 1, wherein the change-sensing means senses the electrical capacitance between the at least one conductor and a second conductor of the strain-sensing means.

3. A system according to claim 1, wherein the change-sensing means senses the electrical resistance of the at least one conductor.

4. A system according to claim 1, wherein the at least one conductor is an inner conductive layer parallel to the innermost layer of the wall, the strain-sensing means further comprising:

an electrical insulating layer parallel to and contacting the inner conductive layer; and an outer conductive layer parallel to and contacting the insulating layer, the inner and outer conductive layers being separated by the insulating layer and defining a capacitive coupling comprising the inner conductive layer, the insulating layer, and the outer conductive layer;

wherein the change-sensing means senses changes in the electrical capacitance of the capacitive coupling resulting from distortion of the wall of the vessel.

5. A system for monitoring a wall of a fluid containment vessel, the wall having an innermost layer for contact with a fluid contained by the vessel and an outermost layer parallel with the innermost layer, the system comprising:

strain-sensing means between the innermost and outermost layers, the strain-sensing means comprising at least one conductor parallel to the innermost layer of the wall;

means for sensing changes in an electrical property associated with the at least one conductor resulting from distortion of the wall of the vessel causing distortion of the at least one conductor, the electrical property being chosen from the group consisting of electrical capacitance and electrical resistance;

wherein the at least one conductor is a helical conductive coil between the innermost and outermost layers and surrounding the innermost layer, the coil defines a helical conductive path along a length of the wall, the helical conductive path has an electrical resistance associated therewith, and the change-sensing means senses changes in the electrical resistance of the helical conductive path resulting from distortion of the wall of the vessel.

6. A system according to claim 5, further comprising:

means for establishing an acceptable range for the electrical resistance; and means for generating a signal that a structural failure of the wall is impending in response to the electrical resistance deviating outside the acceptable range.

7. A system for monitoring a wall of a fluid containment vessel, the wall having an innermost layer for contact with a fluid contained by the vessel and an outermost layer parallel with the innermost layer, the system comprising:

strain-sensing means between the innermost and outermost layers, the strain-sensing means comprising at least one conductor parallel to the innermost layer of the wall;

means for sensing changes in an electrical property associated with the at least one conductor resulting from distortion of the wall of the vessel causing distortion of the at least one conductor, the electrical property being chosen from the group consisting of electrical capacitance and electrical resistance;

wherein the vessel is a hydraulic hose subjected to pressure cycles that induce fatigue in the wall.

8. A system for predicting structural failure of a wall of a hydraulic hose subjected to pressure cycles that induce fatigue in the wall, the wall having an innermost layer for contact with a fluid contained by the vessel and an outermost layer parallel with the innermost layer, the system comprising:

strain-sensing means between the innermost and outermost layers, the strain-sensing means comprising an inner conductive layer parallel to the innermost layer of the wall, an electrical insulating layer parallel to and contacting the inner conductive layer, and an outer conductive layer parallel to and contacting the insulating layer, the inner and outer conductive layers being separated by the insulating layer and defining a capacitive coupling comprising the inner conductive layer, the insulating layer, and the outer conductive layer;

means for sensing changes in the electrical capacitance of the capacitive coupling resulting from distortion of the wall of the vessel;

means for establishing an acceptable range for the electrical capacitance of the capacitive coupling; and means for generating a signal that a structural failure of the wall is impending in response to the electrical capacitance deviating outside the acceptable range.

9. A system according to claim 8, wherein the inner conductive layer, the insulating layer, and the outer conductive layer are continuous along the length and circumference of the hose.

10. A system according to claim 8, wherein each of the inner and outer conductive layers comprises a wire braiding.

11. A system according to claim 8, further comprising a fitting on each of two opposite ends of the hose, each of the fittings having first and second electrically-conductive members that are electrically insulated from each other, the first and second electrically-conductive members being individually electrically connected to one of the inner and outer conductive layers so as to create an electric capacitive charge between the inner and outer conductive layers.

12. A system for predicting structural failure of a wall of a hydraulic hose subjected to pressure cycles that induce fatigue in the wall, the wall having an innermost layer for contact with a fluid contained by the vessel and an outermost layer parallel with the innermost layer, the system comprising:

strain-sensing means between the innermost and outermost layers, the strain-sensing means comprising a helical conductive coil between the innermost and outermost layers and surrounding the innermost layer, the coil defining a helical conductive path along a length of the wall, the helical conductive path having an electrical resistance associated therewith;

means for sensing changes in the electrical resistance of the helical conductive path resulting from distortion of the wall of the hydraulic hose;

means for establishing an acceptable range for the electrical resistance of the helical conductive path; and means for generating a signal that a structural failure of the wall is impending in response to the electrical resistance deviating outside the acceptable range.

13. A system according to claim 12, wherein the conductive coil comprises an electrically-conductive silicone material.

14. A system according to claim 12, wherein the conductive coil comprises a layer of an electrically-conductive silicone material on a layer of an electrically-insulating material.

15. A system according to claim 12, wherein the inner conductive layer, the insulating layer, and the outer conductive layer are continuous along the length and circumference of the hose.

16. A system according to claim 12, wherein each of the inner and outer conductive layers comprises a wire braiding.

17. A system according to claim 12, further comprising a fitting on each of two opposite ends of the hose, each of the fittings having first and second electrically-conductive members that are electrically insulated from each other, the first and second electrically-conductive members being individually electrically connected to one of the inner and outer conductive layers so as to create an electric capacitive charge between the inner and outer conductive layers.

18. A method of predicting structural failure of a wall of a vessel containing a fluid, the method comprising the steps of:
    forming the wall to have an innermost layer for contact with a fluid contained by the vessel, an outermost layer parallel with the innermost layer, and strain-sensing means between the innermost and outermost layers, the strain-sensing means comprising at least one conductor parallel to the innermost layer of the wall;
    sensing changes in an electrical property associated with the at least one conductor resulting from distortion of the wall of the vessel causing distortion of the at least one conductor, the electrical property being chosen from the group consisting of electrical capacitance and electrical resistance;
    establishing an acceptable range for the electrical property; and
    generating a signal that a structural failure of the wall is impending in response to the electrical property deviating outside the acceptable range.

19. A method according to claim 18, wherein the sensing step comprises sensing the electrical capacitance between the at least one conductor and a second conductor of the strain-sensing means.

20. A method according to claim 19, wherein the at least one conductor is formed as an inner conductive layer parallel to the innermost layer of the wall, and the strain-sensing means is formed to further comprise:
    an electrical insulating layer parallel to and contacting the inner conductive layer; and
    an outer conductive layer parallel to and contacting the insulating layer, the inner and outer conductive layers being separated by the insulating layer and defining a capacitive coupling comprising the inner conductive layer, the insulating layer, and the outer conductive layer;
    wherein the sensing step comprises sensing changes in the electrical capacitance of the capacitive coupling resulting from distortion of the wall of the vessel.

21. A method according to claim 18, wherein the sensing step comprises sensing the electrical resistance of the at least one conductor.

22. A method according to claim 18, further comprising subjecting the vessel to fluctuating fluid pressures during the sensing step.

23. A method of monitoring a wall of a vessel containing a fluid, the method comprising the steps of:
    forming the wall to have an innermost layer for contact with a fluid contained by the vessel, an outermost layer parallel with the innermost layer, and strain-sensing means between the innermost and outermost layers, the strain-sensing means comprising at least one conductor parallel to the innermost layer of the wall;
    sensing changes in an electrical property associated with the at least one conductor resulting from distortion of the wall of the vessel causing distortion of the at least one conductor, the electrical property being chosen from the group consisting of electrical capacitance and electrical resistance;
    wherein the at least one conductor is formed as a helical conductive coil between the innermost and outermost layers and surrounding the innermost layer, the coil defines a helical conductive path along a length of the wall, the helical conductive path having an electrical resistance associated therewith, and the method further comprises causing a direct current to flow through the conductive coil and the sensing step comprises sensing changes in the electrical resistance of the helical conductive path resulting from distortion of the wall of the vessel.

24. A method according to claim 23, further comprising the steps of:
    establishing an acceptable range for the electrical resistance; and
    generating a signal that a structural failure of the wall is impending in response to the electrical resistance deviating outside the acceptable range.

25. A system for predicting structural failure of a hydraulic hose, the system comprising:
    a hydraulic hose having:
        an innermost layer for contact with a fluid;
        an outermost layer parallel with the innermost layer;
        an inner conductive layer disposed between the innermost and outermost layers;
        an electrical insulating layer parallel to the inner conductive layer;
        an outer conductive layer parallel to the insulating layer, the inner and outer conductive layers being separated by the insulating layer and defining an electrical property;
    an electrical property monitor in electrical connection with the inner and outer conductive layers of the hydraulic hose; and
    a signal generator in electrical connection with the electrical property monitor, the signal generator generating a signal in response to changes in the electrical property of the hydraulic hose changing as a result of distortion of the innermost layer of the hydraulic hose causing distortion of the inner and outer conductive layers.

26. A system according to claim 25, wherein the electrical property is selected from the group consisting of electrical resistance and electrical capacitance.

27. A system according to claim 25, wherein the signal is a visual signal.

28. A system according to claim 25, wherein the signal is an audible signal.

29. A method of predicting structural failure of a hydraulic hose, the method comprising the steps of:
   providing a hydraulic hose having:
   an innermost layer for contact with a fluid;
   an outermost layer parallel with the innermost layer;
   an inner conductive layer disposed between the innermost and outermost layers;
   an electrical insulating layer parallel to the inner conductive layer;
   an outer conductive layer parallel to the insulating layer, the inner and outer conductive layers being separated by the insulating layer and defining an electrical property selected from the group consisting of electrical capacitance and electrical resistance;
   sensing changes in the electrical property of the hydraulic hose resulting from distortion of the innermost layer causing distortion of the inner conductive layer;
   generating a signal that a structural failure of the wall is impending in response to changes of the electrical property.

30. A method according to claim 29, further comprising establishing an acceptable limit for the electrical property.

31. A method according to claim 30, wherein the signal is generated in response to the electrical property deviating from the acceptable limit.

32. A method according to claim 31, wherein the acceptable limit is a range of values.

33. A method according to claim 31, wherein the acceptable limit is an upper limit.

* * * * *

UNITED STATES PATENT AND TRADEMARK OFFICE
CERTIFICATE OF CORRECTION

PATENT NO. : 7,555,936 B2 Page 1 of 1
APPLICATION NO. : 11/276500
DATED : July 7, 2009
INVENTOR(S) : Gary W. Krutz and Aaron Don Deckard It is certified that error appears in the above-identified patent and that said Letters Patent is hereby corrected as shown below:

Title Page, Item (75) Inventors should read:
--(75) Inventor: Gary W. Krutz, West Lafayette, IN (US)
Aaron Don Deckard, Lexington, KY (US)--.

Signed and Sealed this

Eighteenth Day of May, 2010

David J. Kappos
*Director of the United States Patent and Trademark Office*